United States Patent [19]

Hsu et al.

[11] Patent Number: 4,487,973
[45] Date of Patent: Dec. 11, 1984

[54] HYDROFORMYLATION PROCESS WITH PLATINUM (O) CATALYST

[75] Inventors: Chao-Yang Hsu, Media; Paul E. Ellis, Jr., Downingtown, both of Pa.

[73] Assignee: Sun Tech, Inc., Philadelphia, Pa.

[21] Appl. No.: 491,687

[22] Filed: May 5, 1983

[51] Int. Cl.³ ............................................. C07C 45/50
[52] U.S. Cl. ...................................... 568/454; 568/909
[58] Field of Search ....................... 568/454, 909, 882

[56] References Cited

PUBLICATIONS

Kirk–Othmer, Encyclopedia of Chemical Technology, Third Ed., vol. 16, pp. 637–653.

Primary Examiner—Werren B. Lone
Attorney, Agent, or Firm—J. Edward Hess; Donald R. Johnson; Stanford M. Back

[57] ABSTRACT

Hydroformylation process for preparing aldehydes by reactively contacting an olefin and syngas, at elevated temperature and pressure, in the presence of a catalyst comprising a mixture of (1) a platinum complex of the formula $Pt(QR_3)_m$ where Q is a Group VA element, R is alkyl, alkoxyl, aryl or aryloxyl and m is an integer of from 2 to 4, and (2) a metal halide of the formula $MX_n$ where M is a Group IVB metal, X is a halogen and n is 2 or 4.

10 Claims, No Drawings

HYDROFORMYLATION PROCESS WITH PLATINUM (O) CATALYST

BACKGROUND OF THE INVENTION

This invention relates to catalytic hydroformylation processes for converting olefins to aldehydes.

In the hydroformylation of olefins, carbon monoxide and hydrogen add to the olefin under conditions of elevated temperature and pressure to produce mixtures of linear and branched aldehydes. Catalytic hydroformylation of olefins is known as the "oxo" process. Depending on the olefin type, the catalyst, the solvent and reaction conditions, it is known that selectivity to linear or branched aldehydes, reaction rate and yields can be influenced. For example, cobalt corbonyls and rhodium complexes containing tertiary phosphine or phosphite ligands are known hydroformylation catalysts. See "Oxo Process," Kirk-Othmer, Encyclopedia of Chemical Technology, Third Edition (1981), 16, 637–653; Evans, et al., *J. Chem. Soc., A*, 3133 (1968); and Pruett and Smith, *J. Org. Chem.* 34, 327 (1969). Platinum (II) complexes containing tertiary phosphine are used to obtain higher ratios of straight chain to branched chain aldehydes. See Hsu and Orchin, *J. Amer. Chem. Soc.*, 97, 3553 (1975); Schwager and Knifton, *J. Cat.*, 45, 256 (1976); U.S. Pat. No. 3,981,925 and 3,996,293. Ionic forms of platinum (II) catalysts for hydroformylation of olefins are disclosed in U.S. Pat. Nos. 3,876,672, 4,101,564 and 4,155,939.

However, the platinum (II) catalysts, although somewhat effective in favoring selective formation and high yields of the more desirable straight chain aldehydes, and sometimes at relatively mild conditions of temperature and pressure, nevertheless tend to reduce the reaction rate and therefore diminish the economic importance of the process. Moreover, the large proportion of halides in such catalysts introduces a considerable potential for corrosion of manufacturing equipment, thereby requiring large capital outlays for corrosion resistant equipment and lines, and thus reducing economic value of the catalysts.

SUMMARY OF THE INVENTION

It has now been found that olefins can be catalytically hydroformylated under mild conditions to aldehydes at substantially improved reaction rates with high selectivity and yield of linear aldehydes, and with substantially reduced potential for corrosion, by employing as catalyst a mixture of a platinum (0) complex and a metal halide co-catalyst. The platinum (0) complex may be represented by the formula (1):

$$Pt(QR_3)_m \qquad (1)$$

where Q is a Group VA element, R is akyl, alkoxyl, aryl or aryloxyl, and m is an integer of from 2 to 4. The metal halide co-catalyst may be represented by the formula (2):

$$MX_n \qquad (2)$$

where M is a Group IV B metal, X is a halogen, and n is the integer 2 or 4.

DETAILED DESCRIPTION

In the platinum complex of formula (1), Q preferably is phosphorus, arsenic or antimony and the R groups may be the same or different. R will generally contain 1 to 8 carbon atoms when alkyl or alkoxyl, and 6 to 20 carbon atoms when aryl or aryloxyl, but higher carbon content is possible if desired. "Alkyl" and "alkoxyl" in this specification include cycloalkyl and cycloalkoxyl groups. Also, "aryl" and "aryloxy" in this specification include alkyl-substituted aromatic groups, the entire R group sometimes being referred to as an "alkaryl" or an "alkaryloxyl" group. Typical R groups include methyl, ethyl, hexyl, cyclohexyl, phenyl, naphthyl, tolyl, xylyl, the corresponding hydroxyl substituted groups, and the like. Representative platinum complexes are $Pt(PPh_3)_4$, $Pt[P(OPh)_3]_4$, $Pt(AsPh_3)_4$ and $Pt[P(n-Bu)Ph_2]_4$ where "Ph" is phenyl and "Bu" is butyl.

In the formula (2) for the metal halide co-catalyst, the halogen preferably is chlorine, and M preferably is tin or lead.

Both the platinum complex and the metal halide co-catalyst are known compounds and are commercially available.

The hydroformylation reaction of the invention is generally conducted in a homogeneous liquid reaction medium at elevated temperature and pressure. Preferably, a pressure reactor is charged under an inert gas atmosphere (such as nitrogen) with a solvent, the platinum complex and the metal halide. The catalyst mixture may also be preformed in the solvent prior to charging, if desired. Suitable solvents are inert, non-polar aromatic compounds such as hydrocarbons and oxygen-substituted hydrocarbons. Representative solvents include benzene, toluene, tetraline, xylene (o, m or p) and ketones such as acetone, methylisobutyl ketone and acetophenone. Other solvents may be used, as set forth in the Kirk-Othmer publication and patents cited above. About 10 parts by volume of solvent per part by volume of olefin is sufficient solvent but other amounts may also be used.

The charged mixture is then agitated for a time sufficient to render it homogeneous. Thereafter, the pressure vessel is sealed and purged with syngas (a mixture of hydrogen and carbon monoxide at a mole ratio of about 30:1 to 1:30, preferably about 1:1) and the olefin charged. The amounts of olefin and catalyst may vary widely. Suitable mole ratios are about 50:1 to 10,000:1 of olefin to platinum complex and about 0.5:1 to 1:15 of platinum catalyst to metal halide co-catalyst. The reactor is then charged with syngas to a total pressure of about 100 to 3000 psig, preferably about 500 to 1500 psig, and the temperature is raised to about 50° C. to 125° C., preferably about 75° C. to 110° C. Other temperatures and pressures can be used. The reaction can be followed by removal of samples of product and analysis. Upon completion of reaction, the product can be separated by distillation in the conventional manner. Catalyst solution can be separated and recycled.

The hydroformylation process may be conducted in a batch, semi-continuous or continuous manner. Moreover, the process can be combined with hydrogenation of the aldehydes to alcohols by venting the reactor after aldehyde formation and introducing hydrogen under suitable conditions of temperature and pressure. The catalyst used for the hydroformylation can also be used for the hydrogenation or fresh catalyst can be added. Less preferably, the reactor is not vented and a large volume of hydrogen is introduced for admixture with syngas remaining from the hydroformylation.

The invention is illustrated by the following examples.

EXAMPLE 1

A 300 ml stainless steel autoclave was charged under nitrogen atmosphere with 100 ml of p-xylene, 0.62 g (0.5 mmole) of Pt(PPh$_3$)$_4$ and 0.41 g (1.5 mmole) of SnCl$_4$. After the mixture was stirred for 15 min. under nitrogen atmosphere, the autoclave was sealed, then purged with syngas (H$_2$/CO mole ratio=1:1), and 10.5 g (250 mmole) of propylene was added. The autoclave was then charged to 700 psig of syngas (H$_2$/CO mole ratio=1:1) and quickly heated to 110° C., whereupon the total pressure was adjusted to 1000 psig through constant addition of syngas from a reservoir. Samples of product were removed during the reaction for analysis. After 2 hrs. the reaction was halted, the autoclave cooled, and the liquid mixture analyzed by vapor phase chromatography. Analytical data indicated that the yield of butyraldehyde was 73% and the ratio of n-butyraldehyde to iso-butyraldehyde was 8 to 1, corresponding to 89% of n-butyraldehyde.

EXAMPLES 2-6

In these examples, summarized in Table 1, the reaction procedure is substantially the same as that of Example 1. The main difference is variation of the ratio of SnCl$_2$ or SnCl$_4$ to Pt(PPh$_3$)$_4$. Example 1 results are included for comparison. The results indicate that SnCl$_4$ at higher concentrations gives a faster reaction rate. However, it will be noted that the catalysts of Example 3 and 4 provide higher ratios of straight to branched chain aldehydes.

TABLE 1

| | EXAMPLES | | | | | |
|---|---|---|---|---|---|---|
| | 1 | 2 | 3 | 4 | 5 | 6 |
| REAGENTS | | | | | | |
| Propylene, mmole | 250 | 250 | 244 | 268 | 283 | 248 |
| Pt(PPh$_3$)$_4$, mmole | 0.5 | 0.5 | 0.5 | 0.5 | 0.5 | 0.5 |
| SnX$_n$, mmole | 1.5 | 1.5 | 2.5 | 0.5 | 1.0 | 1.5 |
| | SnCl$_4$ | SnCl$_2$ | SnCl$_2$ | SnCl$_4$ | SnCl$_4$ | SnBr$_4$ |
| p-Xylene, ml. | 100 | 100 | 100 | 100 | 100 | 100 |
| H$_2$/CO (1:1), psig. | 1000 | 1000 | 1000 | 1000 | 1000 | 1000 |
| CONDITIONS | | | | | | |
| Temperature, °C. | 110 | 110 | 110 | 110 | 110 | 110 |
| Reaction Time, hr. | 2 | 2 | 2 | 2 | 2 | 2 |
| RESULTS | | | | | | |
| mmole of C$_4$—aldehydes | 182 | 59 | 86 | 45 | 76 | 40 |
| Ratio of n/iso-butyraldehyde | 89/11 | 94/6 | 95/5 | 95/5 | 92/8 | 93/7 |
| Initial Rate* | 182 | 59 | 86 | 45 | 76 | 40 |

*Initial Rate = mmole of C$_4$—aldehyde/mmole Pt(QR$_3$)$_4$/hr. (calculated from first hr. of reaction)

EXAMPLES 7-11

In these examples, the results of which are summarized in Table 2, a procedure substantially identical to Example 1 was used. The main difference is variation of the phosphine ligand of the platinum complex. Based on rates of reaction, the results indicate that the catalyst of Example 11 is a preferred catalyst. However, the catalyst of Example 7 gives a slightly higher ratio of straight to branched chain aldehydes.

TABLE 2

| | EXAMPLES | | | | |
|---|---|---|---|---|---|
| | 7 | 8 | 9 | 10 | 11 |
| REAGENTS | | | | | |
| Propylene, mmole | 250 | 278 | 299 | 281 | 256 |
| Pt Complex (0.5 mmole) | Pt(PPh$_3$)$_4$ | Pt[P(OPh)$_3$]$_4$ | Pt[P(OPh)$_3$]$_4$ | Pt(AsPh$_3$)$_4$ | Pt[P(n-Bu)Ph$_2$]$_4$ |
| SnCl$_n$, mmole | 1.5 | 1.0 | 1.5 | 1.5 | 1.5 |
| | SnCl$_4$ | SnCl$_4$ | SnCl$_2$ | SnCl$_4$ | SnCl$_4$ |
| p-Xylene, ml. | 100 | 100 | 100 | 100 | 100 |
| H$_2$/CO (1:1), psig. | 1000 | 1000 | 1000 | 1000 | 1000 |
| CONDITIONS | | | | | |
| Temperature, °C. | 110 | 110 | 110 | 80 | 110 |
| Reaction Time, hr. | 2 | 1.5 | 1.5 | 2 | 2 |
| RESULTS | | | | | |
| mmole of C$_4$—aldehydes | 182 | 145 | 153 | 144** | 249 |
| Ratio of n/iso-butyraldehyde | 89/11 | 84/16 | 84/16 | 81/19 | 87/13 |
| Initial Rate* | 182 | 194 | 204 | 144 | 249 |

*mmole of C$_4$—aldehyde/mmole of Pt(QR$_3$)$_4$/hr. calculated from first hr. of reaction
**Includes 48 mmole of dimeric aldehyde

We claim:
1. In a hydroformylation process for preparing aldehydes by reactively contacting, at elevated temperature and pressure, an olefin, hydrogen and carbon monoxide in the presence of a catalyst, the improvement which comprises using as the catalyst a mixture of a platinum complex of the formula:

$$Pt(QR_3)_m$$

where Q is a Group VA element, R is alkyl, alkoxyl, aryl or aryloxyl, and m is an integer of from 2 to 4, and a metal halide co-catalyst of the formula:

$MX_n$ where M is a Group IV B Metal, X is a halogen, and n is 2 or 4.

2. The process of claim 1 wherein Q in the platinum complex is phosphorus, arsenic or antimony.

3. The process of claim 1 wherein, in the co-catalyst, M is tin or lead and X is chlorine.

4. The process of claim 1 wherein the platinum complex is $Pt(PPh_3)_4$.

5. The process of claim 1 wherein the platinum complex is $Pt[P(OPh)_3]_4$.

6. The process of claim 1 wherein the platinum complex is $Pt(AsPh_3)_4$.

7. The process of claim 1 wherein the platinum complex is $Pt[P(n-C_4H_9)Ph_2]_4$.

8. The process of claim 1 wherein the temperature is the range of about 50°–125° C. and the pressure is about 100–3000 psi.

9. The process of claim 1 wherein the temperature is about 75°–110° C., the pressure is about 550–1500 psig, the platinum complex is $Pt(PPh_3)_4$ $Pt[P(OPh)_3]_4$ $Pt(AsPh_3)_4$ or $Pt[P(n-C_4H_9)Ph_2]_4$ and the co-catalyst is $SnCl_2$ or $SnCl_4$.

10. The process of claim 9 wherein the mole ratio of olefin to platinum complex is about 50:1 to 10,000:1 and the mole ratio of platinum complex to co-catalyst is about 0.5:1 to 1:15.

* * * * *